United States Patent [19]

Wust et al.

[11] 4,325,789
[45] Apr. 20, 1982

[54] PROCESS FOR SEPARATING OFF PHENOL FROM A MIXTURE THEREOF WITH A CRESOL

[75] Inventors: Alfredo Wust, Leverkusen; Knut Hammerström, Berg.-Gladbach, both of Fed. Rep. of Germany

[73] Assignee: Bayer Aktiengesellschaft, Leverkusen, Fed. Rep. of Germany

[21] Appl. No.: 117,171

[22] Filed: Jan. 31, 1980

[30] Foreign Application Priority Data

Feb. 8, 1979 [DE] Fed. Rep. of Germany ....... 2904831

[51] Int. Cl.³ .............................................. B01D 3/36
[52] U.S. Cl. ........................................ 203/67; 203/69; 203/70; 568/749
[58] Field of Search ...................... 203/67, 58, 68–70; 568/749, 750, 751, 752

[56] References Cited

FOREIGN PATENT DOCUMENTS 392878 5/1933 United Kingdom ................ 568/750

OTHER PUBLICATIONS

"Azeotropic Data-III", Advances in Chemistry Series 116, pp. 318-323 & pp. 376-383, 1973.

Primary Examiner—Frank Sever
Attorney, Agent, or Firm—Sprung, Felfe, Horn, Lynch & Kramer

[57] ABSTRACT

A process for separating phenol from a mixture of the same with cresol which comprises including in the mixture a component which has a dipole moment of 0 to 0.5 Debye and has a boiling point, under 1 bar, in the temperature range from 120° to 220° C. or which has a dipole moment of 0.5 to 2.5 Debyes and has a boiling point, under 1 bar, in the temperature range from 150° to 190° C. and distilling off phenol together with said component to leave behind said cresol.

8 Claims, 1 Drawing Figure

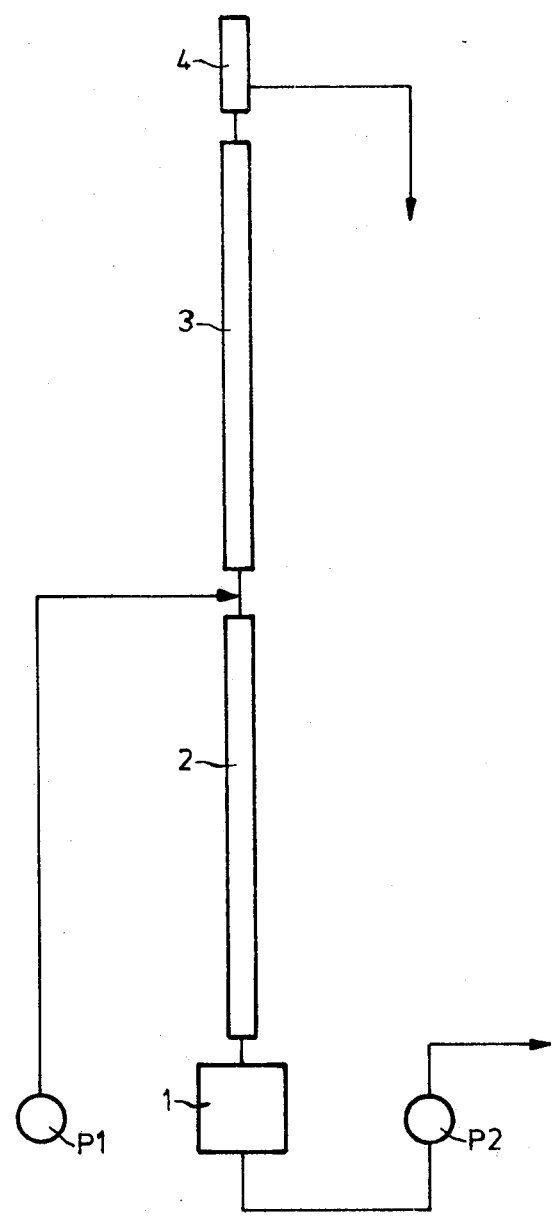

PROCESS FOR SEPARATING OFF PHENOL FROM A MIXTURE THEREOF WITH A CRESOL

The invention relates to a process for separating off phenol from mixtures of cresols.

Separating off phenol from a mixture of isomeric cresols is a troublesome procedure, since the boiling points of the components are close together and separation by distillation is hence made difficult. Since the components are chemically similar, other separation processes, for example chemical separation processes, are very difficult and can scarcely be utilized in industry.

It is particularly difficult to separate off phenol if the contents of phenol which are to be separated off from the cresol are small, for example below 2% by weight, and if the cresol should still contain only a very little phenol, for example less than 0.5% by weight. Small amounts of phenols can be obtained as a by-product, for example, in the preparation of cresols by high temperature saponification of chlorotoluenes using sodium hydroxide solution (U.S. Pat. No. 1,996,744).

A process has now been found for separating off phenol from cresol, which is characterised in that cresol containing phenol is distilled in the presence of a component which has a dipole moment of 0 to 0.5 Debye and has a boiling point, under 1 bar, in the temperature range from 120° to 220° C., or which has a dipole moment of above 0.5 to 2.5 Debyes and has a boiling point, under 1 bar, in the temperature range from 120° to 190° C.

Cresol for the process according to the invention can be ortho-, meta- or para-cresol, or a mixture of the various isomeric cresols.

The components which can be added for the distillation by the process according to the invention generally form an azeotrope with the phenol or with the phenol and the cresol, preferably with the phenol.

Examples which may be mentioned of the additional components for the distillation by the process according to the invention are: optionally halogenated, saturated or unsaturated aliphatic hydrocarbons, cycloaliphatic hydrocarbons, optionally halogenated alkylbenzenes and optionally alkylated halogenophenols.

Optionally halogenated, saturated or unsaturated aliphatic hydrocarbons for the process according to the invention can have a dipole moment of 0 to 0.5 Debye, preferably of 0 to 0.2 Debye, and a boiling point, under 1 bar, of 120° to 220° C., preferably of 150° to 190° C. They are generally straight-chain or branched aliphatic hydrocarbons with about 2 to about 12 carbon atoms. The hydrocarbons can have one or more double bonds and can be substituted by one or more halogen atoms, such as fluorine, chlorine, bromine or iodine, preferably chlorine.

Examples which may be mentioned of optionally halogenated, saturated or unsaturated hydrocarbons are: pentachloroethane, hexachloroethane, octane, decane, dodecane and 1-decene.

Preferred optionally halogenated, saturated or unsaturated hydrocarbons for the process according to the invention are pentachloroethane and n-decane.

Cycloaliphatic hydrocarbons for the process according to the invention can have a dipole moment of 0 to 2 Debyes, preferably of 0 to 1.75 Debyes, and a boiling point, under 1 bar, of 150° to 190° C., preferably of 150° to 180° C. They are generally terpenes.

Examples which may be mentioned of cycloaliphatic hydrocarbons for the process according to the invention are: α-limonene, camphene and α-pinene.

Preferred cycloaliphatic hydrocarbons for the process according to the invention are camphene and α-pinene.

The optionally halogenated alkylbenzene for the process according to the invention can have a dipole moment of 0 to 2.5 Debyes, preferably of 0 to 2.0 Debyes, and a boiling point, under 1 bar, of 150° to 190° C., preferably of 150° to 180° C. It is generally benzene which is substituted by lower (1 to about 6 carbon atoms), straight-chain or branched alkyl radicals and which can be further substituted in the aromatic or aliphatic part of the molecule by one or more halogen atoms, such as fluorine, chlorine, bromine or iodine, but preferably chlorine.

Examples which may be mentioned of optionally halogenated alkylbenzenes for the process according to the invention are: p-dichlorobenzene, o- and p-chlorotoluene, o-, m- and p-bromotoluene, isopropylbenzene, mesitylene, sec.-butylbenzene and methylethylbenzene.

Preferred optionally halogenated alkylbenzenes for the process according to the invention are o- and p-chlorotoluene, mesitylene and methylethylbenzene.

The optionally alkylated halogenophenol for the process according to the invention can have a dipole moment of 0 to 2.5 Debyes, preferably of 0 to 2 Debyes, and a boiling point, under 1 bar, of 150° to 190° C., preferably of 155° to 180° C. It is generally phenol which is substituted by fluorine, chlorine, bromine or iodine, but preferably chlorine, and which can be further substituted by a lower (1 to 6 carbon atoms), straight-chain or branched alkyl radical.

Examples which may be mentioned of optionally alkylated halogenophenols for the process according to the invention are: o-chlorophenol and o-bromophenol.

The preferred optionally alkylated halaogenophenol for the process according to the invention is o-chlorophenol.

It is of course possible to carry out the distillation with a mixture of the components added according to the invention.

The separation in the process according to the invention is preferably carried out as an azeotropic distillation.

The separation in the process according to the invention can be carried out discontinuously or continuously. The component added can be separated off after the separation process and used again in the separation.

The process according to the invention can be carried out, for example, as follows:

The additional component is added to the phenol-containing cresol before the distillation. This can be effected, for example, by introducing the phenol-containing cresol and the additional component separately into the distillation column. In general, 0.01 to 0.4 part, preferably 0.02 to 0.1 part, of the additional component is introduced per one part of the phenol-containing cresol.

The distillation is in general carried out in the temperature range from 120° to 220° C., preferably from 150° to 210° C., and under normal pressure. If the distillation is carried out under another pressure, the temperature ranges of course change accordingly.

During the distillation, the cresol is separated from the phenol and the additional component. The phenol-free cresol can be removed from the bottom of the column. A mixture of phenol and the additional component containing virtually no cresol is obtained over the top of the column.

The mixture obtained over the top of the distillation column can be separated into its constituents in a second distillation column with the aid of an entraining agent for the additional component employed in the separation according to the invention. Examples of entraining agents which may be mentioned are water and n-decane, but preferably water.

On distillation of the phenol, the additional component and the water, pure phenol is obtained at the bottom of the distillation column and a mixture of water, the additional component and in some cases traces of phenol is obtained over the top. After condensing the mixture obtained over the top of the distillation column, a mixture consisting of an aqueous phase and an organic phase is obtained. In the case of a continuous procedure in particular, the aqueous phase is recycled into the second column and the organic phase, which essentially consists of the additional component, is recycled into the first column for the separation, according to the invention, of phenol-containing cresol.

Phenol can be separated from cresol in a simple manner by the process according to the invention. Relatively small amounts of phenol and traces of phenol can easily be separated off from cresol.

Because of the chemical similarity of phenol and cresol, the discovery of additional components by means of which it is possible to separate phenol and cresol by distillation was not to be expected.

BRIEF DESCRIPTION OF DRAWING

Referring to the annexed drawing, the same is a flow diagram showing one embodiment for carrying out the process of the invention.

DESCRIPTION OF SPECIFIC EMBODIMENT

Referring to the appended drawing, the process can be carried out employing a distillation apparatus comprising a column bottom 1, a stripping section 2 and a rectifying section 3. The distillation apparatus can be equipped with a column head 4. Metering pumps P1 and P2 are employed to supply feed to the distillation apparatus and to remove purified cresol. The rectifying section and stripping section can contain customary packing materials and can be evacuated and mirrored. They can contain, for example, four by four mm wire gauge Raschig rings.

EXAMPLES

I. Discontinuous separation of phenol from a mixture of cresols

EXAMPLE 1

435 g of o-chlorotoluene are added to 3,969 g of a mixture of cresol isomers having the analytical composition: less than 0.01% of water, 0.24% of phenol, 25.65% of o-cresol, 50.52% of m-cresol and 23.59% of p-cresol. This mixture is distilled in a 1.2 m long packed column (evacuated and mirrored; 5×5 mm wire gauze Raschig rings) under a vacuum of 400 mbars and at a reflux ratio of 1:10.

The fraction (423 g) which passes over at an overhead temperature of 119° C. contains 1.6% of phenol and is free from o-cresol. Thereafter, the overhead temperature starts to rise and a further fraction is taken off over the top up to 144° C. This subsequent fraction (25 g) consists of 18% of o-chlorotoluene, 4.5% of phenol and 77.5% of o-cresol.

The bottom product (3,914 g) is free from o-chlorotoluene and phenol.

EXAMPLE 2

428 g of p-chlorotoluene are added to 3,747 g of a dehydrated mixture of cresol isomers (composition as in Example 1) with a phenol content of 0.26%.

The distillation is carried out according to the instructions given in Example 1.

The fraction (418 g) which passes over at an overhead temperature of 128° C. contains 2.0% of phenol and is free from o-cresol. The subsequent fraction (27 g) is taken off up to an overhead temperature of 154° C. and is composed of 23% of p-chlorotoluene, 4.8% of phenol and 72.2% of o-cresol.

Neither p-chlorotoluene nor phenol can be detected in the bottom product (3,698 g).

EXAMPLE 3

432 g of a mixture of chlorotoluene isomers (53% of o-chlorotoluene and 47% of p-chlorotoluene) are added to 4,163 g of a dehydrated crude mixture of cresols (composition as in Example 1) with a phenol content of 0.32% and the distillation instructions given in Example 1 are followed.

The fraction (422 g) which passes over at an overhead temperature of 124° to 126° C. is free from o-cresol and contains 2.1% of phenol. The subsequent fraction (24 g) is taken off up to an overhead temperature of 151° C. and consists of 22% of chlorotoluene isomers, 6.3% of phenol and 71.7% of o-cresol.

The bottom product (4,102 g) is free from chlorotoluene isomers and phenol.

II. Continuous separation of phenol from a crude mixture of cresols

EXAMPLE 4

By adding phenol and a mixture of chlorotoluene isomers (53% of o-chlorotoluene and 47% of p-chlorotoluene), a mixture of cresols having the composition: less than 0.01% of water, 0.24% of phenol, 26.09% of o-cresol, 50.71% of m-cresol and 22.96% of p-cresol, is adjusted to a phenol content of 0.5% and a chlorotoluene isomer content of 3.5%.

This mixture is worked up in a distillation apparatus according to the flow diagram of the accompanying drawing.

The phenol-containing cresol and the chlorotoluene are introduced, according to the flow chart, between the rectifying section and the stripping section in an amount of 200 g/hour.

The unit is operated under normal pressure and at a reflux ratio of 1:50.

About 8 g per hour of a mixture of phenol and chlorotoluene isomers which is free from o-cresol are taken off at the top of the apparatus at 156° C. About 190 g of cresol per hour can be removed from the bottom of the column, which is kept at 201° C., also in a continuous procedure.

In the case of this procedure, the bottom product is free from phenol and chlorotoluene isomers.

EXAMPLES 5 to 7

The results of three examples carried out analogously to Example 4 are summarized in the following table. A mixture of cresols having the composition as in Example 4 is used in all cases.

Mesitylene (trimethylbenzene), camphene and p-dichlorobenzene are used instead of chlorotoluene isomers as entraining agents for phenol. The phenol content is in each case 0.5%.

|  | Mesitylene | Camphene | p-Dichloro-benzene |
|---|---|---|---|
| Amount introduced g/hour | 250 | 150 | 200 |
| Concentration of entraining agent in % | 2.5 | 3.0 | 3.0 |
| Top take-off g/hour | 7 | 5 | 7 |
| Bottom discharge g/hour | 240 | 145 | 190 |
| Overhead temperature °C. | 163 | 147 | 135 |
| Bottom temperature °C. | 200 | 202 | 205 |

III. Discontinuous separation of mixtures of phenol and entraining agent using water

EXAMPLE 8

A mixture of 100 g of phenol, 400 g of o-chlorotoluene and 600 g of water is subjected to fractional distillation under normal pressure in a packed column (technical equipment as in Example 1). 926 g of a two-phase mixture of water and o-chlorotoluene are first taken off at a top temperature of 96° C. and at a reflux ratio of 1:10. The aqueous phase is free from phenol, whilst less than 0.04% of phenol can be detected in the o-chlorotoluene phase.

Intermediate runnings are then also distilled off. Distillation is discontinued when the overhead temperature has reached 181° C.

Whilst the intermediate runnings (57 g) are composed of water, o-chlorotoluene and phenol, the bottom product of the column (64 g) consists of pure phenol.

EXAMPLE 9

A mixture of 100 g of phenol, 700 g of water and 700 g of an isomer mixture of 53% of o-chlorotoluene and 47% of p-chlorotoluene is distilled under conditions analogous to those given in Example 8.

1,312 g of a two-phase mixture of water and the two chlorotoluene isomers are taken off over the top at 96° C. Both phases are free from phenol.

The intermediate runnings (a total of 61 g) are likewise distilled off up to an overhead temperature of 181° C. and contain the four components fed in.

The bottom product of the column (55 g) consists of phenol and is free from water and the chlorotoluene isomers.

IV. Continuous separation of mixtures of phenol and entraining agent using water The construction of an apparatus suitable for this separation is similar to that of the unit described in Example 4. The only difference is that the column head 4 is replaced by a condenser with an integrated phase separator. From the separator, it is possible to pass either the upper phase or the lower phase, as desired, into the column as the reflux, whilst the particular phase which remains passes to the discharge. The column is operated under normal pressure.

EXAMPLE 10

A mixture of 500 g of phenol and 100 g of water is initially introduced into the distillation flask 1 according to the diagram. After initially heating, a solution of 800 g of phenol in 3,200 g of a mixture of chlorotoluene isomers (53% of o-chlorotoluene and 47% of p-chlorotoluene) is introduced, at a rate of 150 ml/hour, between the stripping section and rectifying section of the unit via the pump P1. The top distillate obtained is separated into an upper aqueous phase and a lower chlorotoluene phase in the separator. All of the aqueous phase passes to the column as the reflux, whilst the chlorotoluene phase is taken off continuously. At the same time, bottom product is pumped off continuously, whilst maintaining the level in the bottom of the column constant.

After a bottom temperature of 182° C. and an overhead temperature of 96° C. have been established, about 120 ml of chlorotoluene isomers per hour can be taken off at the separator, at a feed rate of 150 ml/hour. In this procedure, the bottom discharge (on average 30 ml/hour) is free from water and chlorotoluene isomers, whilst the phenol content of the chlorotoluene isomers passing over is 1 to 2%.

EXAMPLE 11

The same apparatus is used as in Example 10.

A mixture of 500 g of phenol and 100 g of water is initially introduced into the distillation flask and, after initial heating, a solution of 800 g of phenol in 3,200 g of mesitylene is introduced into the apparatus as described.

The top condensate is separated into an upper mesitylene phase and a lower aqueous phase in the separator. The mesitylene is taken off continuously, whilst the water is recycled to the column as the reflux.

After establishing all the parameters (bottom temperature: 182° C., overhead temperature: 95° C., feed: 190 ml/hour, top take-off 160 ml/hour and bottom take-off 30 ml/hour), the bottom product is free from water and mesitylene. The mesitylene obtained in the separator contains 2 to 3% of phenol.

EXAMPLE 12

The apparatus described in Example 10 is used.

A mixture of 100 g of n-decane and 500 g of dehydrated crude cresol isomers is initially introduced into the distillation flask. The composition of the crude cresol is similar to that described in Example 1.

After initial heating, 200 ml per hour of crude cresols of the above composition are metered continuously into the unit between the stripping section and rectifying section. The column is operated under normal pressure.

The bottom temperature is brought to 205° C., and an overhead temperature of 157° C. is thereby established.

A two-phase mixture, with n-decane as the upper phase and phenol as the lower phase, is obtained in the separator. Each of the two phases contains about 10% of the other components.

The n-decane phase is recycled to the column as the reflux, whilst the phenol phase is drained off from time to time.

With a feed of 200 ml/hour, on average 0.5 ml/hour of phenol phase can be taken off at the separator. The bottom discharge (about 200 ml/hour) is free from phenol.

EXAMPLE 13

The apparatus and procedure are as described in Example 12.

Instead of n-decane, a hydrocarbon cut (170° to 175° C. under normal pressure) which is obtained by fractionation of white spirit in a 1.2 m long packed column at a reflux ratio of 1:10, is used.

An upper hydrocarbon phase and a lower phenol phase are obtained in the separator. The hydrocarbon phase is recycled as the reflux and the phenol phase is taken off.

After constant experimental conditions have been established (the temperatures and flow rates correspond to the data indicated in Example 12), the bottom discharge is free from phenol and hydrocarbons. The phenol phase from the separator contains on average 51% of hydrocarbons.

EXAMPLE 14

A mixture of 900 g of phenol and 100 g of n-decane is initially introduced into a distillation flask. Distillation is then carried out under normal pressure over a 1.2 m long packed column (as described in Example 1), which is provided with a condenser with an integrated phase separator.

The phenol phase which separates out is recycled to the column as the reflux and the n-decane phase is taken off. The distillation is discontinued as soon as no further phase separation takes place in the separator. The bottom product is then free from n-decane.

The phenol content of the n-decane phase taken off is on average 10.5%.

What is claimed is:

1. A process for separating phenol from the mixture of the same with ortho cresol which comprises adding to the mixture a component selected from the group consisting of:
   A. A halogenated, saturated or unsaturated aliphatic hydrocarbon or a non-halogenated saturated or unsaturated aliphatic hydrocarbon with a dipole moment of 0 to 0.5 Debye and a boiling point, under 1 bar, of 120° to 220° C.;
   B. A cycloaliphatic hydrocarbon with a dipole moment of 1 to 2 Debyes which has a boiling point, under 1 bar, of 150° to 190° C.;
   C. A halogenated alkyl benzene or a non-halogenated alkyl benzene with a dipole moment of 0 to 2.5 Debyes which has a boiling point, under 1 bar, or 150° to 190° C.; and
   D. A alkylated halogenophenol or a non-alkylated halogenophenol with a dipole moment of 0 to 2.5 Debyes which has a boiling point, under 1 bar, of 150° to 190° C. and distilling off phenol together with said component to leave behind said ortho cresol.

2. A process according to claim 1 wherein said component is a non-halogenated or halogenated, saturated or unsaturated aliphatic hydrocarbon with a dipole moment of 0 to 0.5 Debye and a boiling point, under 1 bar, of 120° to 220° C.

3. A process according to claim 1 wherein said component is a cycloaliphatic hydrocarbon with a dipole moment of 0 to 2 Debyes and has a boiling point, under 1 bar, of 150° to 190° C.

4. A process according to claim 1 wherein said component is a non-halogenated or halogenated alkylbenzene with a a dipole moment of 0 to 2.5 Debyes and has a boiling point, under 1 bar, of 150° to 190° C.

5. A process according to claim 1 wherein said component is a non-alkylated or alkylated halogenophenol with a dipole moment of 0 to 2.5 Debyes and a boiling point, under 1 bar, of 150° to 190° C.

6. A process according to claim 1 wherein said distillation is an azeotropic distillation.

7. A process according to claim 1, wherein said component is an optionally halogenated alkyl benzene with a dipole moment of 0 to 2.5 Debyes which has a boiling point, under 1 bar, of 150° to 190° C. and said optionally halogenated alkyl benzene is selected from the group consisting of optionally halogenated alkyl benzene having a straight or branched alkyl radical with 1 to 6 carbon atoms which can be optionally substituted with fluorine, chlorine, bromine or iodine.

8. A process according to claim 7, wherein said optionally halogenated alkyl benzene is selected from the group consisting of o-chlorotoluene, p-chlorotoluene, o-bromotoluene, m-bromotoluene, p-bromotoluene, isopropylbenzene, mesitylene, sec.-butylbenzene and methylethylbenzene.

* * * * *